United States Patent [19]
Berry

[11] 3,999,943
[45] Dec. 28, 1976

[54] SEMI-CONTINUOUS PROCESS FOR ALTERNATELY PRODUCING A STERILIZING VAPOR AND REGENERATING A DILUTE PROCESS SOLUTION IN A SINGLE APPARATUS

[75] Inventor: Jean-Luc Berry, Mesnil sur L'Estree, France

[73] Assignee: E. P. Remy et Cie, Dreux, France

[22] Filed: Jan. 25, 1974

[21] Appl. No.: 436,662

Related U.S. Application Data

[63] Continuation of Ser. No. 166,735, July 28, 1971, abandoned.

[30] Foreign Application Priority Data

Aug. 7, 1970  France .............................. 70.29315

[52] U.S. Cl. .................................. 21/108; 203/18; 203/93; 203/96; 203/97; 424/343
[51] Int. Cl.² ......................................... A61L 9/04
[58] Field of Search ................. 203/95, 96, 97, 92, 203/93, 18; 55/54; 21/56, 57, 94, 118, 108, 109, 110, 74 R; 424/343

[56] References Cited

UNITED STATES PATENTS

| | | | |
|---|---|---|---|
| 1,881,718 | 10/1932 | Lawrie | 203/96 |
| 2,960,447 | 11/1960 | Anderson et al. | 203/96 |
| 3,493,323 | 2/1970 | Demuth | 21/74 R |

*Primary Examiner*—Frank W. Lutter
*Assistant Examiner*—Frank Sever
*Attorney, Agent, or Firm*—Kenyon & Kenyon Reilly Carr & Chapin

[57] ABSTRACT

The method of the invention consists in conveying a concentrated aqueous solution of a substance less volatile than water and miscible with the latter into the upper portion of a liquid-vapor exchange column operating at atmospheric pressure and supplied with saturated water vapor at its lower portion, in collecting a dilute aqueous solution of said substance in the lower portion of said column and vapor rich in said substance and sparingly rich in water, at a temperature comprised between about 110° and 150° C, in the upper portion of the said column, said column also alternately functioning to dehydrate, and thereby regenerate said dilute aqueous solution to thereby produce said concentrated aqueous solution.

3 Claims, 4 Drawing Figures

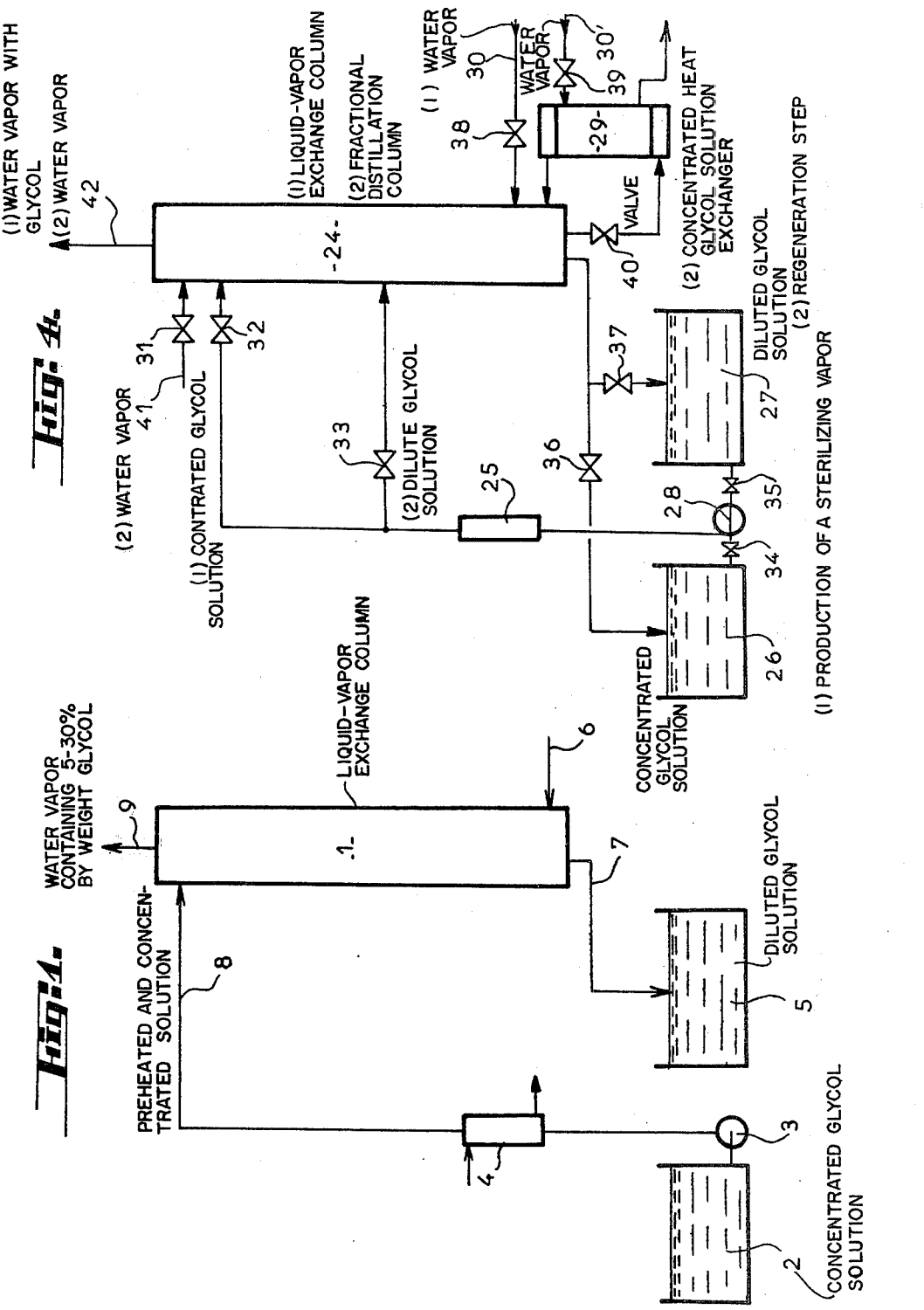

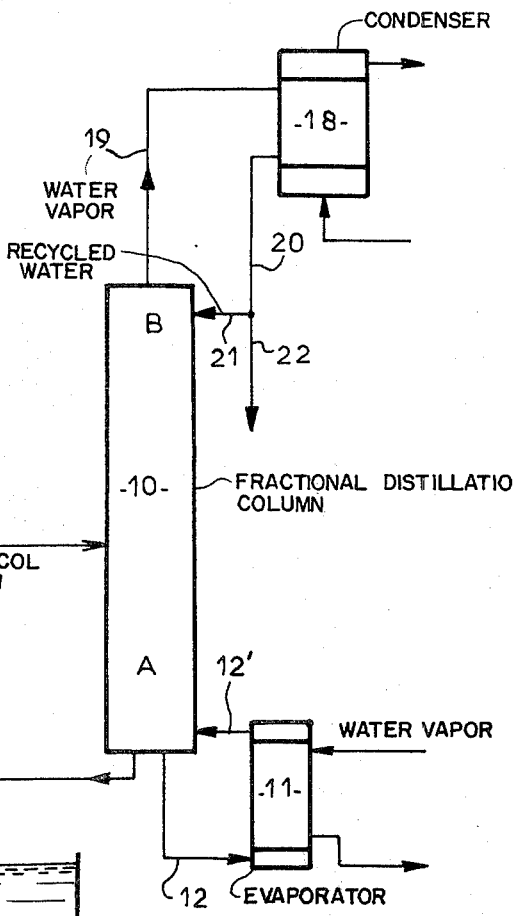
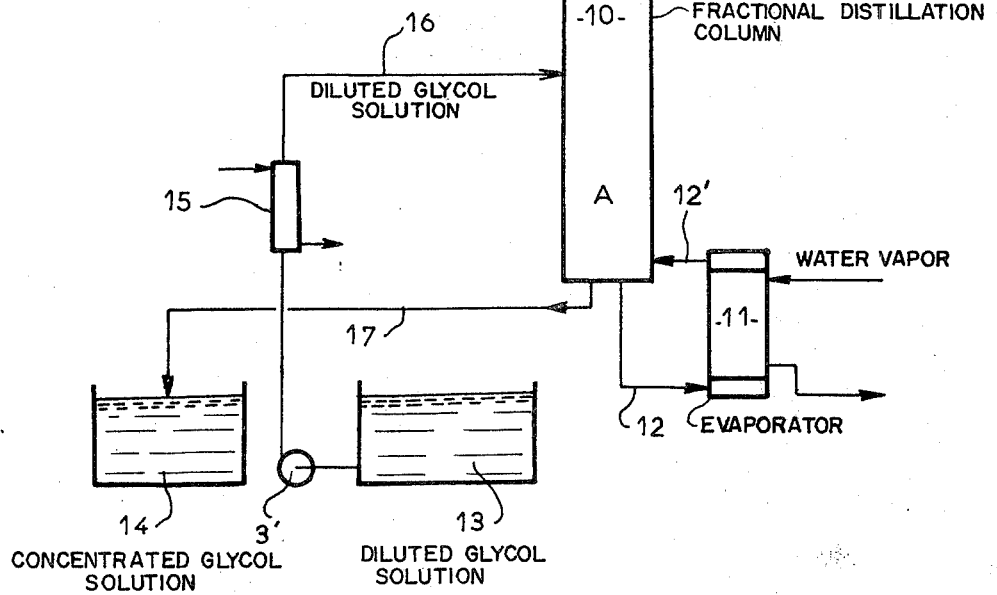

SEMI-CONTINUOUS PROCESS FOR ALTERNATELY PRODUCING A STERILIZING VAPOR AND REGENERATING A DILUTE PROCESS SOLUTION IN A SINGLE APPARATUS

This is a continuation, of application Ser. No. 166,735 filed July 28, 1971, now abandoned.

The saturated vapor rich in said substance may be used for sterilizing purposes.

The present invention relates to a method for rapidly producing water vapor rich in sparingly volatile substance. More specifically, the present invention concerns a method for obtaining rapidly and at a high rate-of-flow saturated vapor containing water and a substance which, in the liquid state, is less volatile than water, and miscible with the latter, for instance poly-alcohols, and therefore capable of reaching temperatures comprised between 110° and 150° C at atmospheric pressure, thus enabling containers, devices, machines and plants to be efficiently sterilized by thermal means according, in particular, to the method described in U.S. Pat. application No. 155,420 filed on June 22, 1971 now U.S. Pat. No. 3,762,874 in the name of the applicant.

The saturated vapor resulting from the practice of this invention directly deliverable to the sterilizing locale or plant of said U.S. patent via pipes 9 or 42.

The usual known methods for producing vapor from a mixture of water with a sparingly volatile substance by way of boiling have the drawback of requiring the use of an evaporator working with a hot source, the temperature of which, in particular, is higher than that of the desired vapor. Moreover, the said evaporator is heated by water vapor and is subjected to very high pressures on the order of, for instance, from 15 to 20 bars, so that the construction of such an evaporator is extremely expensive. Direct heating of the evaporator by means of gas or by means of a resistor entails similar drawbacks and, in addition, serious fire risks.

From another point of view, the use of the said known methods for sterilization purposes requires rapid production of considerable flows of vapor at a high temperature and low pressure, especially at atmospheric pressure. It is known that in using the usual methods, large-surface and, therefore, high-capacity evaporators must be available, thus compelling the use of a great amount of non-volatile product during the starting-up period and waiting until the said product reaches its boiling point.

Therefore, it is not possible in practice to have immediately available a considerable flow of vapor rich in a substance such as a poly-alcohol.

On the contrary, the method according to the invention enables such a result to be obtained.

The said method is characterized in that it consists in conveying a concentrated aqueous solution of the said substance into the upper portion of a liquid-vapor exchange column or overheating column under atmospheric pressure and fed with water vapor under atmospheric pressure at its lower portion, in collecting the dilute aqueous solution of the said substance in the lower portion of the said column and vapor rich in the said substance and not rich in water, at a temperature comprised between about 110° C. and 150° C, in the upper portion of the said column.

The sterilizing and high-boiling-point substances at which the invention is more particularly directed are for instance poly-alcohols such as monoethylene-glycol (boiling point: 198° C), diethylene-glycol (boiling point: 245° C), triethylene-glycol (boiling point: 276° C), propylene-glycol (boiling point: 189° C) and glycerol (boiling point: 290° C, with decomposition).

According to a preferred form of embodiment of the present invention, the concentrated solution of the said substance is pre-heated in liquid phase before being conveyed into the column; preferably, the process is so conducted as to carry the temperature of the said substance to a value comprised between 100° C and 120° C.

According to a preferred form of embodiment of the present invention, use is made, as a sterilizing substance, of monoethylene-glycol, designated hereinafter by the term glycol, and the method is so conducted as to obtain, in the upper portion of the over-heating column, vapor which is rich in the said substance, at a temperature comprised between 120° C and 140° C, at atmospheric pressure.

According to another feature of the invention, the method is so carried out as to alternately produce vapor rich in the said substance and regenerate the concentrated solution of the said substance from the dilute solution, the said regeneration being performed by conveying the dilute solution into the same column which, in this step is operated as a conventional fractional distillation column. To this end it comprises a section for the concentration of the sparingly volatile substance, at the bottom of which calories are supplied and concentrated solution is extracted, and a section for water concentration, at the top of which vapor which is very dilute in the said substance, or water vapor, is extracted, care being taken to modify in an appropriate manner the positions of the feed-in and draw-off points as well as the nature of the phases passing at the said points.

The operation of the column in the case where the aforesaid sparingly volatile substance is glycol will now be explained. by coming into contact with the liquid phase, which rapidly reaches its boiling temperature when descending through the column, the vapor which rises in counter-current becomes loaded with glycol and the chemical equilibrium resulting from the affinity between glycol and water leads to an increase of glycol concentration in the vapor phase. As the pressure remains constant, the temperature increases rapidly as the vapor rises, so that in the upper portion of the column, vapor at atmospheric pressure is available whose temperature corresponds to the characteristics set forth above.

The invention will be better understood and other objects, characteristics and advantages thereof will appear as the following description proceeds, with reference to the appended drawings given solely by way of example illustrating one form of embodiment of the invention and wherein:

FIG. 1 shows a plant for the carrying out of the method of rapid production of vapor rich in sparingly volatile substance according to the present invention;

FIG. 2 shows a plant connected with that of FIG. 1 for the carrying out of an already known conventional regeneration process which is advantageously combined according to the invention with the said method of production;

FIG. 3 shows the upper portion of the regeneration column of the plant of FIG. 2, according to a modified form of embodiment;

FIG. 4 shows a unitary plant for the carrying out of a combined method according to the present invention, for alternate rapid production of vapor rich in sparingly volatile substance and regeneration of the dilute aqueous solutions of the said substance.

There is seen in FIG. 1 a column 1, the structure of which is similar to that of any usual distillation column, the said column being for instance equipped with a series of plates of a known type, sufficient in number to provide the conditions of enrichment with sparingly volatile substance. For the sake of simplification, it will be assumed in the following description made with reference to FIGS. 1 to 4, that the said sparingly volatile substance is constituted by glycol.

The plant comprises a glycol tank 2 in which this substance is stored in concentrated aqueous solution at any temperature, a force or pressure pump 3 and a heat exchanger 4 used as a heater for the concentrated glycol solution; the heat source of the heater 4 may be water vapor at any pressure, usually water vapor in the conditions in which it is produced in industrial plants. The plant also comprises a tank 5 intended to receive the dilute glycol solution collected at the bottom of the column 1.

The plant operates as follows: water vapor, preferably at atmospheric pressure, i.e., at 100° C. is conveyed through the duct 6 into the bottom of the column 1, at the same time as a concentrated glycol solution is conveyed through the duct 8 into the upper portion of column 1, after being heated to, for instance, 100° to 120° C by passing through the heater 4; the dilute glycol solution collected at the bottom of column 1 is conveyed into the tank 5 through the duct 7; thus, vapor at a temperature of from 120° to 140° C containing between about 5% and about 30% by weight glycol is available in the upper portion of the column through the duct 9.

It will be noted that when the circuit of water vapor at 100° C and at atmospheric pressure is established through the overheating column, it is sufficient, in order to considerably raise the temperature, to convey into the top of the column a concentrated glycol solution which may not be at boiling temperature, this operation requiring only the pump 3 to be operated.

Likewise, if the needs in vapor at atmospheric pressure and a temperature higher than 100° C are satisfied, it is sufficient to stop the force pump 3.

Of course, the said plant may be provided with any suitable supervision and/or regulation means, which means are not shown in the Figure for the sake of clarity.

The method and plant of FIG. 1 may be achieved by adopting one or several of the following variants:

a. pre-heating of the concentrated glycol solution in the tank 2, outside the periods of production of vapor rich in glycol;

b. use of a concentrated glycol solution without preheating in heater 4: indeed, it is not indispensable to carry the solution to a temperature approximating that of boiling in order that the temperature of the vapor phase in the column be increased between the bottom and the top of the column;

c. the by weight ratio of the concentrated glycol solution rate-of-flow to the water vapor rate-of-flow may vary considerably depending upon the temperatures sought for. For guidance, this ratio is often comprised between 0.5 and 4, but varies preferably between about 1 and about 3 for temperatures on the order of from 120° to 140° C; of course, the method is not limited by such values, more especially as the latter are specific to the case where the substance considered is monoethylene-glycol.

d. pre-heating of the concentrated glycol solution through heat exchange between the latter and the dilute glycol solution issuing from the column and flowing into the tank 5.

The plant of FIG. 2 comprises essentially a conventional fractional distillation column 10 with a section of enrichment and exhaustion, with respect to glycol, of a dilute ethylene-glycol solution. The plant comprises an evaporator 11 whose hot circuit is supplied with external water vapor, the phase subjected to evaporation being constituted by a concentrated glycol solution drawn off at the bottom of the column 10 through the duct 12, the vapor phase formed in the evaporator 11 being conveyed through the duct 12' into the bottom of the column 10. The plant comprises a tank 3' containing the dilute glycol solution to be regenerated, a force or pressure pump 3' for the said solution and a heat exchanger 15 serving to preheat the dilute glycol solution, which is conveyed, subsequent to pre-heating in the exchanger 15, between the concentration and exhaustion sections of the column 10 through the duct 16; a duct 17 serves to draw off the concentrated glycol solution from the bottom of the column 10 and convey it into the tank 14. A condenser 18 whose cold circuit is constituted by water serves to condense the vapor collected from the duct 19, at the top of the regeneration column 10, the condensate collected through the duct 20 being partially recycled at the top of the column 10 through the duct 21 and partially extracted from the system through the duct 22; the said condensate is constituted by water with almost no glycol.

The lower section A of column 10 performs the glycol concentration of the liquid phase, whereas the upper section B performs the water concentration of the vapor phase, i.e., its exhaustion with respect to glycol. The calories necessary for the operation of the column are essentially supplied by the evaporator 11.

FIG. 3 illustrates an advantageous variant of FIG. 2, wherein the condenser 18 is dispensed with; this case specifically corresponds to such conditions that the product obtained at the top of the column is sufficiently dilute with respect to glycol to be considered as being water; the water vapor issuing from the duct 19' (replacing, at the top of the column, the duct 19 of FIG. 2) may then be used outside the plant for any suitable purposes; in this case, a supply of hot or cold liquid water is provided through the duct 23 at the top of the column 10' so as to compensate for the absence of the recycling which takes place through the duct 21 in the case of FIG. 2.

The plants of FIGS. 1 and 2 are advantageously coupled, according to the present invention, by supplying the tank 13 of the plant of FIG. 2, by means of the tank 5 of the plant of FIG. 1 and the tank 2 of the latter plant by the tank 14 of the plant of FIG. 2; of course, the tanks 5 and 13 may form one and the same reserve container for a dilute glycol solution and the tanks 2 and 14 may form one and the same reserve container for the concentrated glycol solution.

A more advantageous manner of associating the glycol-rich vapor production means and the dilute glycol-solution concentration means, in order to reduce the capital and upkeep costs of the equipment, consists in using the plant shown in FIG. 4, which plant comprises a single column 24 whose structure is designed as a conventional distillation column with a glycol supply and exhaustion section, the said column being associated with a heater 25, a tank 26 for the concentrated glycol solution, a tank 27 for the dilute glycol solution, a force or pressure pump 28 and an evaporator 29 fed from a circuit of water vapor at atmospheric pressure supplied through the duct 30'; stop valves 31 to 40 are arranged at the locations shown in FIG. 4 on the various ducts of the plant.

Such a plant is designed to operate alternately for the production of vapor rich in glycol and for the regeneration of a dilute glycol solution, in which case the column 4 operates alternately and correspondingly as a column similar to column 1 of FIG. 1, and then as a regeneration column in a manner similar to column 10 of FIG. 2 (or column 10' of FIG. 3).

During the glycol-rich vapor production stage at 120°–140° C, which vapor escapes through the duct 42, the valves 31, 33, 35, 36, 39 and 40 are closed, the valves 32, 34, 37 and 38 are open; it will be observed that under such conditions the plant operates in the same manner as that of FIG. 1 if water vapor is supplied through the duct 30 and if the concentrated ethylene-glycol solution is conveyed from the tank 26 into the heater 25 by means of the force pump 28.

If now the valves 31 (provided on the water-supply duct 41), 33, 35, 36, 39 and 40 are open and the valves 32, 34, 37 and 38 are closed, it is observed that the plant of FIG. 4 can operate, under the same conditions as those of FIG. 2 or preferably those of FIG. 3 in the example considered, so as to perform the concentration, with respect to glycol, of the dilute solution of the latter contained in the tank 27, by conveying the said solution into the heater 25, starting the pump 28 and conveying the water vapor into the evaporator 29; vapor which is very dilute with respect to glycol or water vapor according to the selected operating parameters is thus obtained in the duct 41; the plant may operate uninterruptedly for, alternately, rich vapor production and concentration, or it may be used only at certain moments for either rich vapor production or concentration. Such a plant is adapted, as that of FIG. 1 or as that of FIG. 1 associated with that of FIG. 2 or that of FIG. 3, to provide almost instantaneously, for instance, in a few seconds time, at the desired rate and under the desired conditions of use, glycol-rich vapor which may be used, in particular, to sterilize closed spaces, enclosures, articles or apparatuses of any kind whatsoever, at the desired moment, during the desired period and at any desired rate. For instance, the sterilization may last about one hour when the plant of FIG. 3 is operated to produce vapor rich in glycol, with storage of the dilute glycol solution issuing from the column; regeneration of the concentrated glycol solution may be spread over the remainder of the day by re-using the dilute glycol solution formed during the sterilizing operation and storing the concentrated glycol solution for the following sterilizing operation.

The plant according to the invention may comprise other usual auxiliary devices such as condensers, heat exchangers, supervision or regulation devices, etc., especially a heat exchanger for heat recovery between the solution entering and the solution issuing from the column, etc.

Of course, the invention is by no means limited to the forms of embodiment described and illustrated which have been given by way of example only. In particular, it comprises all means constituting technical equivalents to the means described as well as their combinations, if the latter are carried out according to the spirit of the invention.

What is claimed is:

1. A semi-continuous process for alternately producing a sterilizing vapor and regenerating a dilute process solution, said process comprising, alternately operating a single apparatus in separate, intermittent sterilizing vapor production and re-generation modes, said sterilizing vapor production mode consisting of the steps of:
    a. feeding an aqueous concentrate of a substance selected from the group consisting of mono-ethylene glycol, di-ethylene glycol, tri-ethylene glycol, propylene glycol and glycerol to the upper portion of a vapor/liquid contact column operating at substantially atmospheric pressure,
    b. feeding saturated steam at atmospheric pressure to the lower portion of said vapor-liquid contact column;
    c. withdrawing a dilute aqueous solution of said substance from the lower portion of said vapor/liquid contact column,
    d. withdrawing a sterilizing vapor substantially saturated with said substance from the upper portion of said vapor/liquid contact column;
    said vapor being at a temperature of about 100° to 150° C;
    said regeneration mode consisting of the steps of:
    e. feeding at least a portion of said aqueous dilute solution of step (c) to an intermediate portion of said vapor/liquid contact column;
    f. reboiling at least a portion of the liquid in the bottom of said vapor/liquid contact column;
    g. withdrawing a vapor fraction consisting essentially of water vapor from the upper portion of said vapor/liquid contact column, and
    h. withdrawing a liquid consisting essentially of said substance of step (a) from the lower portion of said liquid-vapor contact column.

2. The process of claim 1, wherein the sterilizing vapor produced thereby, contains a substance selected from the group recited in claim 1.

3. The process of claim 2, wherein said substance is monoethylene glycol, the weight percentage of said monoethylene glycol in said sterilizing vapor being between 5 and 30%.

* * * * *